United States Patent
Ichikawa

(10) Patent No.: US 11,500,458 B2
(45) Date of Patent: Nov. 15, 2022

(54) ELECTRONIC APPARATUS, METHOD FOR CONTROLLING THE ELECTRONIC APPARATUS, AND STORAGE MEDIUM

(71) Applicant: CANON KABUSHIKI KAISHA, Tokyo (JP)

(72) Inventor: Sho Ichikawa, Ebina (JP)

(73) Assignee: Canon Kabushiki Kaisha, Tokyo (JP)

( * ) Notice: Subject to any disclaimer, the term of this patent is extended or adjusted under 35 U.S.C. 154(b) by 11 days.

(21) Appl. No.: 16/902,606

(22) Filed: Jun. 16, 2020

(65) Prior Publication Data

US 2020/0393898 A1 Dec. 17, 2020

(30) Foreign Application Priority Data

Jun. 17, 2019 (JP) .............................. JP2019-112314

(51) Int. Cl.

| A61B 3/113 | (2006.01) |
| G03B 13/02 | (2021.01) |
| G03B 13/16 | (2021.01) |
| G03B 13/36 | (2021.01) |
| G06F 3/13 | (2006.01) |

(Continued)

(52) U.S. Cl.
CPC .............. *G06F 3/013* (2013.01); *A61B 3/113* (2013.01); *G03B 13/04* (2013.01); *G03B 13/36* (2013.01); *G06F 3/03547* (2013.01)

(58) Field of Classification Search
USPC ....................................................... 348/78
See application file for complete search history.

(56) References Cited

U.S. PATENT DOCUMENTS

| 2008/0080846 A1 | 4/2008 | Grip |
| 2011/0249165 A1 | 10/2011 | Churei |

(Continued)

FOREIGN PATENT DOCUMENTS

| JP | 2001-100903 A | 4/2001 |
| JP | 2015-022208 A | 2/2015 |
| JP | 2018-037893 A | 3/2018 |

OTHER PUBLICATIONS

Turner et al, "Combining gaze with manual interaction to extend physical reach", 1st International Workshop on Pervasive Eye Tracking & Mobile Eye-Based Interaction, Pet Mei, 2011, pp. 33-36, , Beijing, China.

*Primary Examiner* — Patricia I Young

(74) *Attorney, Agent, or Firm* — Canon U.S.A., Inc. I.P. Division

(57) ABSTRACT

A reception unit receives an eye direction input that is an input based on an eye tracking process, and a control unit controls movement of a selected position based on an operation on an operation member. The control unit performs control such that, in a first state in which the selected position is not designated based on the eye direction input, the selected position is moved, in response to the operation member being operated by a predetermined operation amount, by a first amount from a position set before the operation member is operated, and that, in a second state in which the selected position is designated based on the eye direction input, the selected position is moved, in response to the operation member being operated by the predetermined operation amount, by a second amount smaller than the first amount from a position based on the eye direction input.

17 Claims, 7 Drawing Sheets

(51) Int. Cl.
*G06F 3/01* (2006.01)
*G03B 13/04* (2021.01)
*G06F 3/0354* (2013.01)

(56) References Cited

U.S. PATENT DOCUMENTS

| | | |
|---|---|---|
| 2014/0204029 A1 | 7/2014 | Lopez |
| 2014/0258942 A1 | 9/2014 | Gershom |
| 2017/0083145 A1* | 3/2017 | Ichikawa ............ G06F 3/04883 |
| 2017/0155825 A1* | 6/2017 | Yoshikawa ............ H04N 5/772 |
| 2018/0234621 A1 | 8/2018 | Oyama |

* cited by examiner

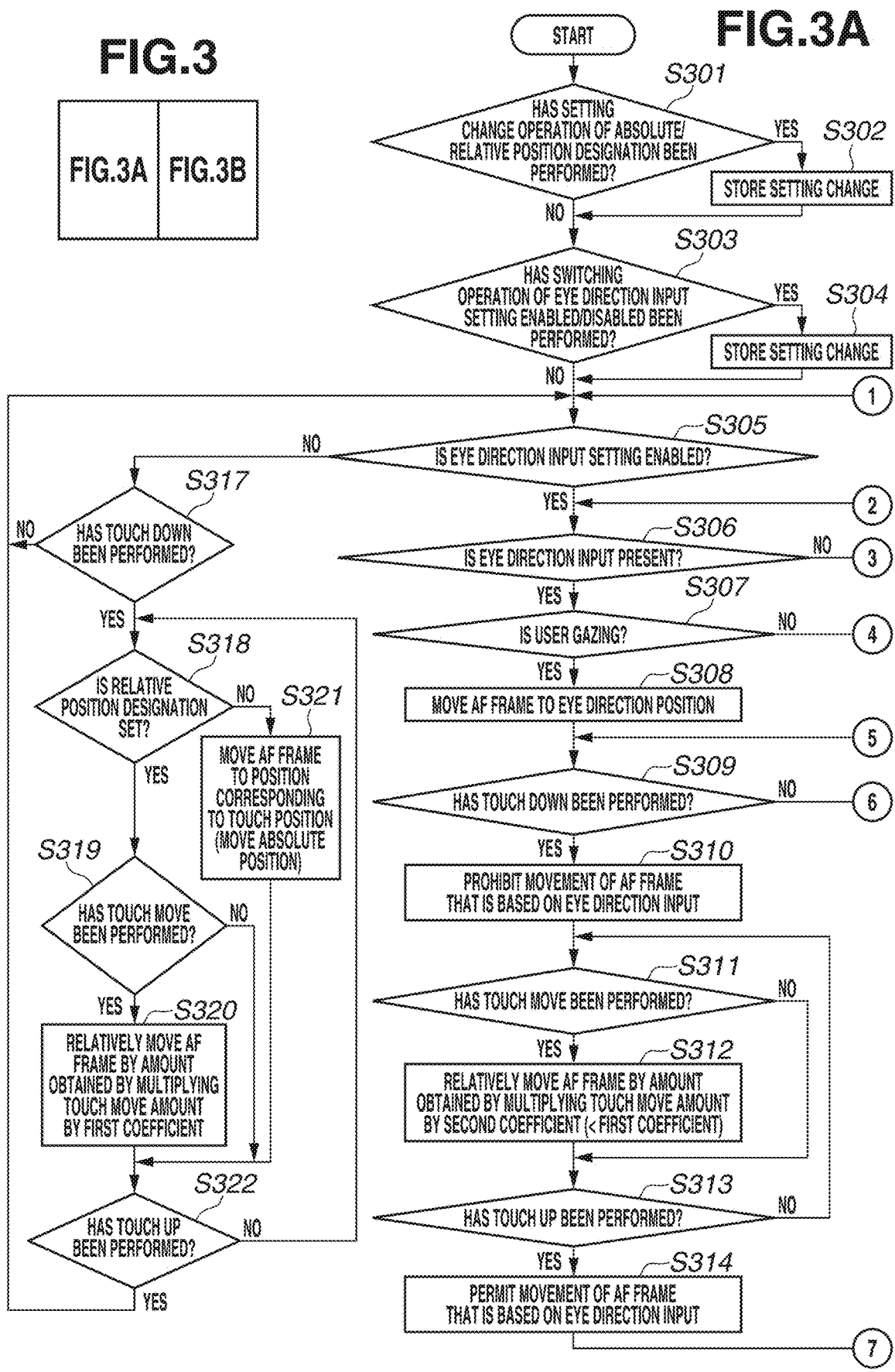

ELECTRONIC APPARATUS, METHOD FOR CONTROLLING THE ELECTRONIC APPARATUS, AND STORAGE MEDIUM

BACKGROUND OF THE INVENTION

Field of the Invention

The present invention relates to an electronic apparatus, a method for controlling the electronic apparatus, and a storage medium, and particularly to an electronic apparatus that can perform eye-tracking, a method for controlling the electronic apparatus, and a storage medium.

Description of the Related Art

There has been conventionally proposed a camera that detects an eye direction (line of sight) of a photographer, or a user, detects a region (position) at which the photographer is looking at in a field of view of a viewfinder, and controls an image capturing function, such as autofocusing. Japanese Patent Application Laid-Open No. 2015-22208 discusses a technique for detecting a position at which the user's eye is directed (eye direction position) while the user is looking into a viewfinder, and displaying an autofocus (AF) frame at the eye direction position. Japanese Patent Application Laid-Open No. 2015-22208 discusses that the displayed eye direction position can be moved by the user operating an operation member operable in eight directions of a camera main body, in a case where the eye direction position is not a position desired by the user.

There has been proposed a method for enabling various settings including the above-described function with a touch operation while the user is looking into a viewfinder, by using a display unit provided on the outside of the viewfinder as a touchpad. Japanese Patent Application Laid-Open No. 2018-037893 discusses that the user can optionally set a setting related to a touch operation for operating a touchpad while looking into a viewfinder, to either absolute position designation or relative position designation. When the absolute position designation is set, an AF frame can be displayed at a position corresponding to a Touch-Down position. When the relative position designation is set, an AF frame can be moved in accordance with the detection of a Touch-Move operation, without displaying the AF frame at a position corresponding to a Touch-Down position.

In Japanese Patent Application Laid-Open No. 2015-22208, if an AF frame position displayed when no eye direction is input is distant from a position desired by the user, a large number of operations is required for moving the AF frame to the position desired by the user. In Japanese Patent Application Laid-Open 2018-037893, the AF frame is displayed at a touch position when the setting related to a Touch-Move operation is set to the absolute position designation. Thus, it is difficult to perform a fine movement operation of the AF frame. When the setting related to a Touch-Move operation is set to the relative position designation, it is difficult to perform fine adjustment if a movement amount of the AF frame with respect to a Touch-Move amount is large, and the number of operations increases if a movement amount of the AF frame is small. This is not limited to the case of moving the AF frame, and the same applies to the case of selecting a position for a certain purpose.

SUMMARY OF THE INVENTION

In view of the foregoing, the present invention is directed to enabling a selected position to be moved swiftly and accurately to a position desired by a user.

According to an aspect of the invention, an electronic apparatus includes at least one memory and at least one processor which function as a reception unit configured to receive an eye direction input that is an input based on an eye tracking process, and a control unit configured to control movement of a selected position based on an operation on an operation member. The control unit performs control such that, in a first state in which the selected position is not designated based on the eye direction input, the selected position is moved, in response to the operation member being operated by a predetermined operation amount, by a first amount from a position set before the operation member is operated, and that, in a second state in which the selected position is designated based on the eye direction input, the selected position is moved, in response to the operation member being operated by the predetermined operation amount, by a second amount smaller than the first amount from a position based on the eye direction input.

Further features of the present invention will become apparent from the following description of exemplary embodiments with reference to the attached drawings.

BRIEF DESCRIPTION OF THE DRAWINGS

FIG. 3 including FIGS. 3A and 3B are a flowchart illustrating control processing based on an eye direction input and a touch operation that are related to a display position of an autofocus (AF) frame according to an exemplary embodiment of the present invention.

DESCRIPTION OF THE EMBODIMENTS

An exemplary embodiment of the present invention will be described in detail below with reference to the accompanying drawings.

It is to be noted that the following exemplary embodiment is merely one example for implementing the present invention and can be appropriately modified or changed depending on individual constructions and various conditions of apparatuses to which the present invention is applied. Thus, the present invention is in no way limited to the following exemplary embodiment.

Hereinafter, exemplary embodiments of the present invention will be described with reference to the accompanying drawings.

Figure 1A:
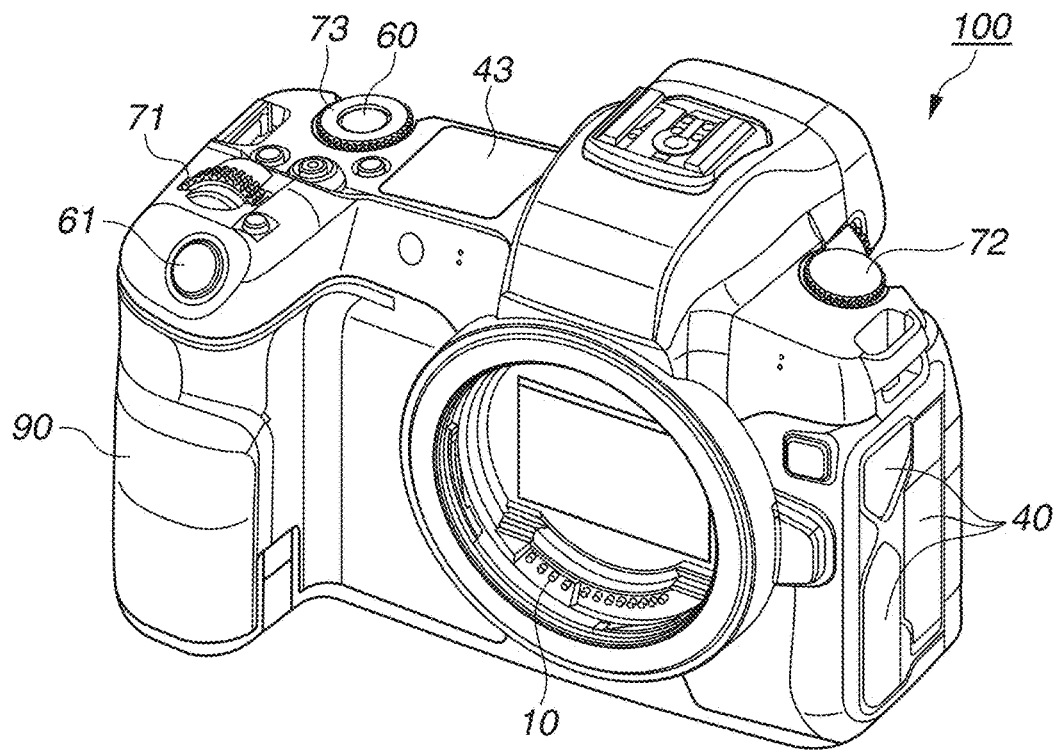
FIGS. 1A and 1B are external views illustrating a digital camera according to an exemplary embodiment of the present invention.
Figure 1B:
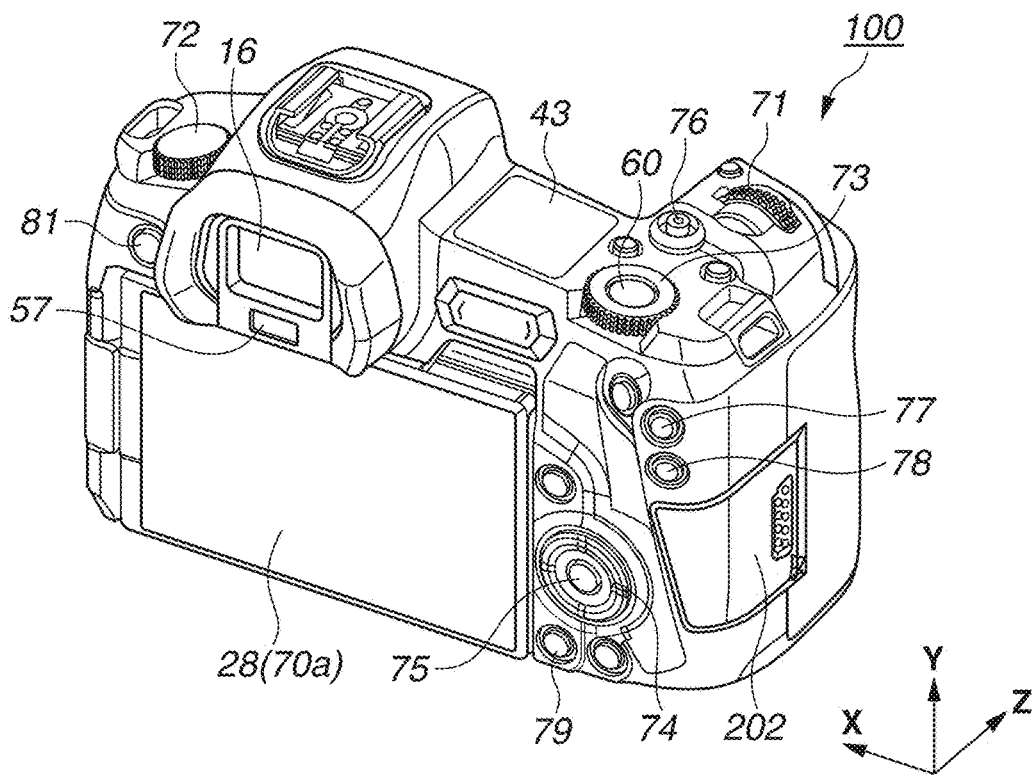

FIGS. 1A and 1B are external views illustrating a digital camera 100 serving as an example of an apparatus to which the present invention can be applied. FIG. 1A is a front side perspective view of the digital camera 100 and FIG. 1B is a back side perspective view of the digital camera 100. In FIGS. 1A and 1B, a display unit 28 is provided on the camera back side that displays images and various types of information. A touch panel 70a is capable of detecting a touch operation performed on a display surface (operation surface) of the display unit 28. A viewfinder external display unit 43 is provided on a camera top surface. Various setting values of a camera including shutter speed and aperture value are displayed on the viewfinder external display unit 43. A shutter button 61 is an operation unit for issuing an image capturing instruction. A mode selection switch 60 is an operation unit for switching between various modes. A terminal cover 40 is a cover that protects a connector (not illustrated) connecting the digital camera 100 and a connection cable for connecting with an external device. A main electronic dial 71 is a rotary operation member included in an operation unit 70. By rotating the main electronic dial 71, setting values, such as shutter speed and aperture value, can be changed. A power switch 72 is an operation member for switching between ON and OFF of the power of the digital camera 100. A sub electronic dial 73 is a rotary operation member included in the operation unit 70, and can move a selected frame and feed an image.

A cross key 74 is an operation member included in the operation unit 70 and including a push button that can be pressed in four directions. An operation can be performed in accordance with a direction in which the cross key 74 is pressed. A SET button 75 is a push button included in the operation unit 70, and is used mainly for determining a selected item. A movie button 76 is used for issuing instructions to stop or move image capturing (recording). An auto-exposure (AE) lock button 77 is included in the operation unit 70, and can fix an exposure state by being pressed in an image capturing standby state. An enlargement button 78 is included in the operation unit 70 and is an operation button for switching between ON and OFF of an enlarged mode in live view display of an image capturing mode. The operating of the main electronic dial 71 after turning the enlarged mode ON enlarges or reduces a live view image. In a reproduction mode, the enlargement button 78 functions as an enlargement button for enlarging a reproduced image and increasing an enlargement ratio. A reproduction button 79 is included in the operation unit 70, and is an operation button for switching between the image capturing mode and the reproduction mode. The pressing of the reproduction button 79 while the digital camera 100 is in the image capturing mode shifts the digital camera 100 to the reproduction mode, and displays the latest image among images recorded on a recording medium 200, on the display unit 28. A menu button 81 is included in the operation unit 70. By the menu button 81 being pressed, a menu screen on which various settings is settable is displayed on the display unit 28. The user can intuitively perform various settings using the menu screen displayed on the display unit 28, the cross key 74, and the SET button 75. A communication terminal 10 is used for the digital camera 100 to perform communication with a lens unit 150 (attachable and detachable, described below). An eyepiece unit 16 is an eyepiece unit of an eyepiece viewfinder (look-in viewfinder). The user can visually check a video displayed on an internal electric viewfinder (EVF) 29 via the eyepiece unit 16. An eye-proximity detection unit 57 is a sensor that detects whether an eye of a user is in proximity to the eyepiece unit 16. A lid 202 is a lid of a slot storing the recording medium 200. A grip portion 90 is a holding portion having a shape that can be easily grasped by a right hand when the user holds the digital camera 100. The shutter button 61 and the main electronic dial 71 are arranged at positions operable by the index finger of the right hand in a state in which the digital camera 100 is held by the little finger, the ring finger, and the middle finger grasping the grip portion 90. In addition, the sub electronic dial 73 is arranged at a position operable by the thumb of the right hand in the same state.

Figure 2:
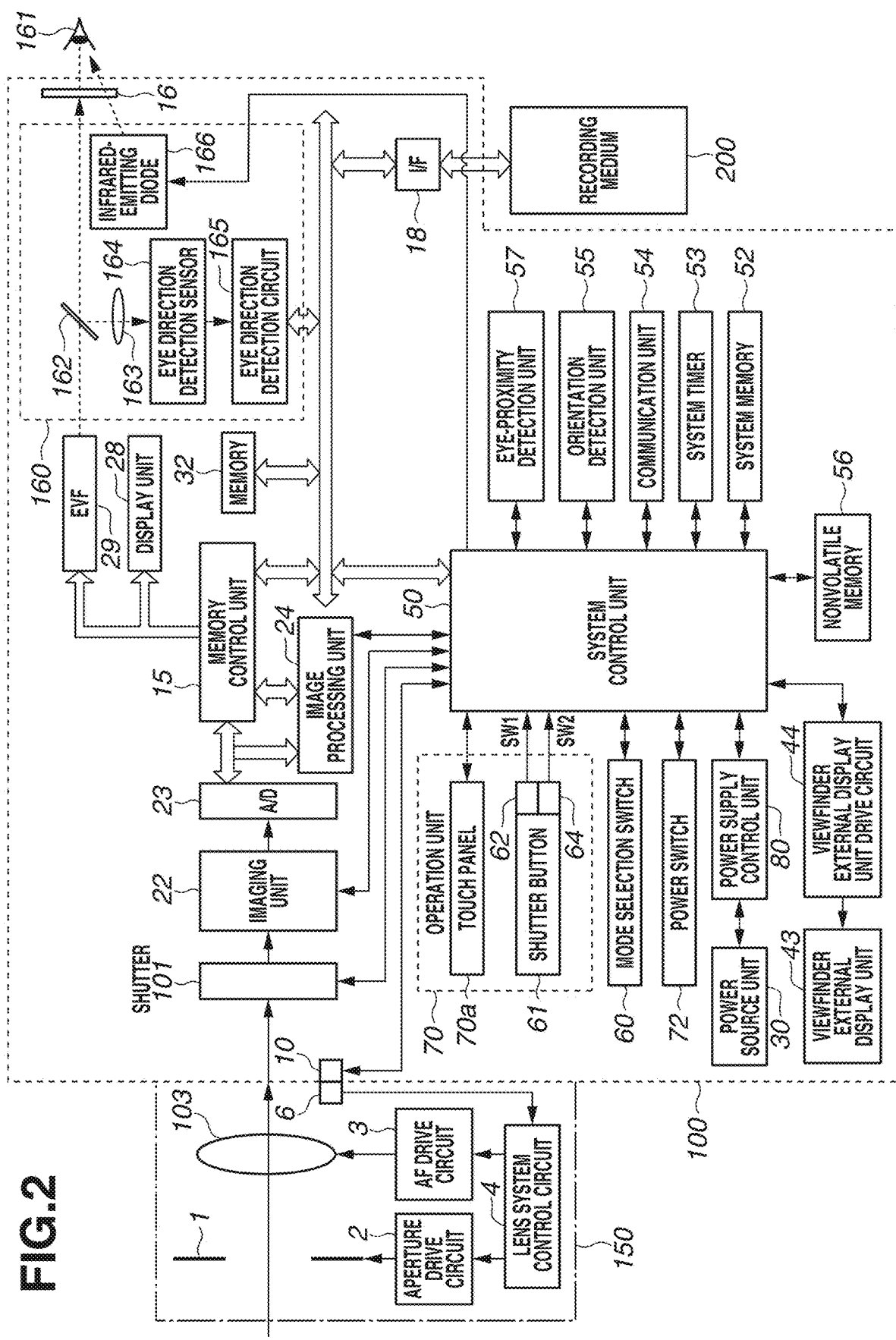
FIG. 2 is a block diagram illustrating a configuration of the digital camera according to an exemplary embodiment of the present invention.

FIG. 2 is a block diagram illustrating a configuration example of the digital camera 100 according to the present exemplary embodiment. In FIG. 2, the lens unit 150 is a lens unit including an interchangeable imaging lens. While a lens 103 normally includes a plurality of lenses, the plurality of lenses is simplified and only one lens is illustrated in FIG. 2. A communication terminal 6 is a communication terminal for the lens unit 150 to perform communication with the digital camera 100. The lens unit 150 communicates with a system control unit 50 via the communication terminal 6 and the above-described communication terminal 10, and controls an aperture 1 via an aperture drive circuit 2 using an internal lens system control circuit 4. After that, a focus is adjusted by the displacement of the lens 103 via an autofocus (AF) drive circuit 3.

A shutter 101 is a focal plane shutter that can freely control an exposure time of an imaging unit 22 under the control of the system control unit 50.

The imaging unit 22 is an image sensor including a charge-coupled device (CCD) sensor or a complementary metal-oxide semiconductor (CMOS) sensor that converts an optical image into an electrical signal. An analog-to-digital (A/D) converter 23 is used for converting an analog signal output from the imaging unit 22, into a digital signal.

An image processing unit 24 performs resize processing, such as predetermined pixel interpolation or reduction, and color conversion processing on data from the A/D converter 23 or data from a memory control unit 15 (described below). The image processing unit 24 also performs predetermined calculation processing using data about a captured image. The system control unit 50 performs exposure control and ranging control based on the calculation result obtained by the image processing unit 24. Through-the-lens (TTL) system AF processing, AE processing, and electronic flash preliminary emission (EF) processing are thereby performed. The image processing unit 24 further performs predetermined calculation processing using data about a captured image, and also performs TTL system automatic white balance (AWB) processing based on the obtained calculation result.

The memory control unit 15 controls data transmission and reception between the A/D converter 23, the image processing unit 24, and a memory 32. Output data from the A/D converter 23 is directly written into the memory 32 via the image processing unit 24 and the memory control unit 15, or via the memory control unit 15. The memory 32 stores image data obtained by the imaging unit 22 and converted by the A/D converter 23 into digital data, and image data to be displayed on the display unit 28 or the EVF 29. The memory 32 has a storage capacity sufficient for storing a predetermined number of still images, and a predetermined time length of a moving image and voice.

In addition, the memory 32 also serves as a memory (video memory) for image display. Image data for display that has been written into the memory 32 is displayed on the display unit 28 or the EVF 29 via the memory control unit 15. The display unit 28 and the EVF 29 perform display in accordance with a signal from the memory control unit 15, on a display device, such as a liquid crystal display (LCD) or an organic electroluminescence (EL) display. Pieces of data having been once A/D-converted by the A/D converter 23 and stored in the memory 32 are sequentially transferred to the display unit 28 or the EVF 29 and displayed thereon. A live view display (LV display) can be thus performed. Hereinafter, an image displayed as a live view will be referred to as a live view image (LV image).

An infrared-emitting diode 166 is a light emitting element for detecting a position at which the user's eye (line of sight) is directed in a viewfinder screen (eye direction position), and emits infrared light onto an eyeball (eye) 161 of the user in proximity to the eyepiece unit 16. The infrared light emitted from the infrared-emitting diode 166 is reflected on the eyeball (eye) 161, and the reflected infrared light reaches a dichroic mirror 162. The dichroic mirror 162 reflects only infrared light and lets through visible light. The reflected infrared light for which the optical path is changed forms an image on an imaging plane of an eye direction detection sensor 164 via an image forming lens 163. The image forming lens 163 is an optical member included in an eye tracking optical system. The eye direction detection sensor 164 includes an imaging device, such as a CCD image sensor.

The eye direction detection sensor 164 photoelectrically converts the incident reflected infrared light into an electrical signal, and outputs the electrical signal to an eye direction detect circuit 165. The eye direction detect circuit 165 includes at least one processor, detects the eye direction position from an image or the movement of the eyeball (eye) 161 of the user, based on an output signal of the eye direction detection sensor 164, and outputs detected information to the system control unit 50. In this manner, an eye tracking block 160 includes the dichroic mirror 162, the image forming lens 163, the eye direction detection sensor 164, the infrared-emitting diode 166, and the eye direction detect circuit 165.

In the present invention, the eye direction is detected by a method called a conical reflection method using the eye tracking block 160. In the corneal reflection method, the eye direction and the eye direction position is detected from a positional relationship between a pupil of the eyeball (eye) 161 and reflected infrared light that has been emitted from the infrared-emitting diode 166 and reflected especially by a cornea of the eyeball (eye) 161. Aside from the conical reflection method, there are various methods for detecting the eye direction and the eye direction position, such as a method called a limbus reflection method in which a difference in reflectance between a black part and a white part of an eye is utilized. An eye tracking method other than the above-described methods may be used as long as the eye direction and the eye direction position can be detected.

On the viewfinder external display unit 43, various setting values of a camera including shutter speed and aperture value are displayed via a viewfinder external display unit drive circuit 44.

A nonvolatile memory 56 is an electrically-erasable/recordable memory, and for example, a flash read-only memory (ROM) is used. Constants for operating the system control unit 50 and programs are stored in the nonvolatile memory 56. The programs refer to computer programs for executing various flowcharts to be described below in the present exemplary embodiment.

The system control unit 50 is a control unit including at least one processor or circuit, and controls the entire digital camera 100. By executing the above-described program recorded in the nonvolatile memory 56, the system control unit 50 implements each piece of processing in the present exemplary embodiment, which will be described below. For example, a random access memory (RAM) is used as a system memory 52. Constants for operating the system control unit 50, variables, and programs read out from the nonvolatile memory 56 are loaded onto the system memory 52. In addition, the system control unit 50 also performs display control by controlling the memory 32 and the display unit 28.

A system timer 53 is a time measuring unit for measuring a time used for various types of control or a time of a built-in clock.

The mode selection switch 60, a first shutter switch 62, a second shutter switch 64, and the operation unit 70 each serve as an operating member for inputting various operation instructions to the system control unit 50. The mode selection switch 60 switches an operation mode of the system control unit 50 to either a still image capturing mode or a moving image capturing mode. The still image capturing mode includes an automatic image capturing mode, an automatic scene determination mode, a manual mode, an aperture priority mode (Av mode), a shutter speed priority mode (Tv mode), and a program AE mode (P mode). The still image capturing mode further includes as various scene modes having different image capturing settings for respective image capturing scenes, and a custom mode. The user can directly switch an operation mode to any of these modes with the mode selection switch 60. Alternatively, an operation mode may be switched in the following manner. The mode selection switch 60 once switches a screen to a list screen of image capturing modes. Then, any of a plurality of displayed modes is selected using another operation member so that an operation mode is switched to the selected mode. In a similar manner, the moving image capturing mode may include a plurality of modes.

The first shutter switch 62 is turned ON during the operation of the shutter button 61 provided on the digital camera 100. That is to say, the first shutter switch 62 is turned ON by so-called half press (i.e. an image capturing preparation instruction), and generates a first shutter switch signal SW1. In response to the first shutter switch signal SW1, an image capturing preparation operation, such as AF processing, AE processing, AWB processing, and EF processing, is started.

The second shutter switch 64 is turned ON upon the completion of an operation of the shutter button 61. That is to say, the second shutter switch 64 is turned ON by so-called full press (i.e. image capturing instruction), and generates a second shutter switch signal SW2. In response to the second shutter switch signal SW2, the system control unit 50 starts operations of a series of image capturing processes starting from the readout of a signal from the imaging unit 22 up to writing of a captured image onto the recording medium 200 as an image file.

The operation unit 70 includes various operation members each serving as an input unit for receiving operations from the user. The operation unit 70 at least includes the following operation unit: the shutter button 61, the touch panel 70a, the main electronic dial 71, the power switch 72, the sub electronic dial 73, the cross key 74, the SET button 75, the movie button 76, the AE lock button 77, the enlargement button 78, the reproduction button 79, and the menu button 81.

A power supply control unit 80 includes a battery detection circuit, a direct current (DC)-DC converter, and a switch circuit for switching a block to be supplied with power. The power supply control unit 80 detects whether or not a battery is attached, the type of the battery, and remaining battery capacity. In addition, the power supply control unit 80 controls the DC-DC converter based on a detection result and an instruction from the system control unit 50, and supplies necessary voltage to components including the recording medium 200 for a necessary time period. A power source unit 30 includes a primary battery, such as an alkaline battery and a lithium battery, a secondary battery, such as a nickel-cadmium (NiCd) battery, a nickel-metal hydride (NiMH) battery, and a lithium (Li) battery, and an alternating current (AC) adapter.

A recording medium interface (I/F) 18 is an interface to the recording medium 200, such as a memory card and a hard disc. The recording medium 200 is, for example, a memory card for recording a captured image, and includes a semiconductor memory or a magnetic disc.

A communication unit 54 is connected wirelessly or via a wired cable, and transmits or receives a video signal and an audio signal. The communication unit 54 can also be connected with a wireless local area network (LAN) and the Internet. In addition, the communication unit 54 can be connected with an external device also via Bluetooth (registered trademark) or Bluetooth Low Energy. The communication unit 54 can transmit an image (including a live view) captured by the imaging unit 22 and an image recorded on the recording medium 200. The communication unit 54 can also receive images and other various types of information from an external device.

An orientation detection unit 55 detects the orientation of the digital camera 100 with respect to a direction of gravitational force. Based on the orientation detected by the orientation detection unit 55, it can be determined whether an image captured by the imaging unit 22 is an image captured with the digital camera 100 which is held in a traverse direction or an image captured with the digital camera 100 which is held in a longitudinal direction. The system control unit 50 can add orientation information corresponding to the orientation detected by the orientation detection unit 55, to an image file of an image captured by the imaging unit 22, or record an image with the image rotated. As the orientation detection unit 55, an acceleration sensor or a gyro sensor can be used. Using the acceleration sensor or the gyro sensor serving as the orientation detection unit 55, the movement (pan, tilt, lifting, whether stationary, etc.) of the digital camera 100 can also be detected.

The eye-proximity detection unit 57 is an eye-proximity detection sensor that detects the proximity of the eye (object) to eyepiece unit 16 of the viewfinder (eye-proximity) and the separation of the eye 161 from the eyepiece unit 16 (eye-separation) (proximity detection). The system control unit 50 switches the display (displayed state)/non-display (non-displayed state) of the display unit 28 and the EVF 29 based on the state detected by the eye-proximity detection unit 57. More specifically, if at least the digital camera 100 is in an image capturing standby state, and a switching setting of a display destination of a live view image captured by the imaging unit 22 is set to an automatic switching setting, when the eye 161 is not in close-proximity to the eyepiece unit 16, the display destination is set to the display unit 28 and the display is set to ON, and the EVF 29 is brought into the non-displayed state. When the eye 161 is in close proximity to the eyepiece unit 16, the display destination is set to the EVF 29 and the display is set to ON, and the display unit 28 is brought into the non-displayed state. For example, an infrared light proximity sensor can be used as the eye-proximity detection unit 57. The eye-proximity detection unit 57 can detect the proximity of a certain object to the eyepiece unit 16 of the viewfinder incorporating the EVF 29. When an object is brought into close proximity to the sensor, infrared light projected from a light projection unit (not illustrated) of the eye-proximity detection unit 57 is reflected and received by a light receiving unit (not illustrated) of the infrared light proximity sensor. A distance between the object and the eyepiece unit 16 (eye proximity distance) can also be determined based on an amount of the received infrared light. In this manner, the eye-proximity detection unit 57 performs eye-proximity detection of detecting a proximity distance of an object to the eyepiece unit 16. In the present exemplary embodiment, the light projection unit and the light receiving unit of the eye-proximity detection unit 57 are assumed to be devices different from the above-described infrared-emitting diode 166 and the eye direction detection sensor 164. The infrared-emitting diode 166 however may also serve as the light projection unit of the eye-proximity detection unit 57. In addition, the eye direction detection sensor 164 may also serve as the light receiving unit. If an object that comes near the eyepiece unit 16 within a predetermined distance from the eyepiece unit 16 from an eye-non-proximity state in which the eye 161 is not in the proximity to the eyepiece unit 16 (non-proximity state) is detected, it is assumed here that the eye-proximity is detected. If an object for which the proximity to the eyepiece unit 16 is detected is separated from the eyepiece unit 16 by a predetermined distance or more from the eye-proximity state (proximity state), it is assumed here that the eye-separation is detected. A threshold for detecting the proximity of the eye and a threshold for detecting the eye-separation may be different from each other by providing hysteresis, for example. In addition, after the proximity of the eye is detected, it is assumed that the eye stays in the eye-proximity state until the separation of the eye is detected. After the separation of the eye is detected, it is assumed that the eye stays in the eye-non-proximity state until the approximation of the eye is detected. The infrared light proximity sensor is an example, and another sensor may be employed as the eye-proximity detection unit 57 as long as the sensor can detect the proximity of an eye or an object that can be regarded as the proximity of the eye.

The system control unit 50 can detect the following operations or states based on outputs from the eye tracking block 160.

- An operation of newly inputting (detecting) an eye direction of a user whose eye is in the proximity to the eyepiece unit 16, i.e., the start of an eye direction input.
- A state in which the eye direction input of the user whose eye is in the proximity to the eyepiece unit 16 is being input.
- A state in which the user whose eye is in the proximity to the eyepiece unit 16 is gazing.
- An operation in which the user whose eye is in the proximity to the eyepiece unit 16 looks away, i.e., the end of an eye direction input.
- A state in which no eye direction of the user whose eye is in the proximity to the eyepiece unit 16 is input.

The gaze described herein refers to a case where a movement amount of the eye direction position of the user does not exceed a predetermined movement amount within a predetermined time.

The touch panel 70a and the display unit 28 can be integrally formed. For example, the touch panel 70a is configured to have light transmittance that does not disturb display on the display unit 28, and is attached to the top layer of a display surface of the display unit 28. Input coordinates on the touch panel 70a and display coordinates on the display screen of the display unit 28 are associated with each other. This structure can provide a graphical user interface (GUI) that performs display as if the user could directly operate a screen displayed on the display unit 28. The system control unit 50 detects the following operations performed on the touch panel 70a or the states thereof.

- An operation of a finger or a stylus that has not been in touch with the touch panel 70a newly touching the touch panel 70a, i.e., the start of a touch on the touch panel 70a (hereinafter, referred to as "Touch-Down").
- A state in which a finger or a stylus is in touch with the touch panel 70a (hereinafter, referred to as "Touch-On").
- An operation of a finger or a stylus moving over the touch panel 70a with the finger or stylus in touch with the touch panel 70a (hereinafter, referred to as "Touch-Move").
- The detachment of a finger or a stylus that has been in touch with the touch panel 70a, i.e., the end of a touch on the touch panel 70a (hereinafter, referred to as "Touch-Up").
- A state in which nothing touches the touch panel 70a (hereinafter, referred to as "Touch-Off").

If the Touch-Down is detected, the Touch-On is detected at the same time. After the Touch-Down, normally, the Touch-On continues to be detected until the Touch-Up is detected. The Touch-Move is detected in the state in which the Touch-On is detected. Even if the Touch-On is detected, the Touch-Move is not detected unless a touch position moves. After the Touch-Up of all the fingers or styluses that have been in touch is detected, the Touch-Off is detected.

These operations and states, and position coordinates on the touch panel 70a at which a finger or a stylus is in touch are notified to the system control unit 50 via an internal bus. The system control unit 50 determines what type of operation (touch operation) has been performed on the touch panel 70a based on the notified information. As for the Touch-Move, a moving direction of a finger or a stylus moving on the touch panel 70a can also be determined for each perpendicular component and horizontal component on the touch panel 70a based on a change in position coordinates. If it is detected that the Touch-Move is performed for a predetermined distance or more, it is determined that a slide operation has been performed. An operation of swiftly moving a finger by a certain amount of distance with the finger in touch with a touch panel, and detaching the finger in this state will be referred to as a flick. In other words, the flick is an operation of swiftly moving the finger over the touch panel 70a like a flip. If it is detected that the Touch-Move has been performed at a predetermined speed or more for a predetermined distance or more, and the Touch-Up is detected in this state, it can be determined that a flick has been performed (it can be determined that a flick has been performed subsequent to the slide operation). Furthermore, a touch operation of simultaneously touching a plurality of points (e.g. two points), and bringing the touch positions closer to each other will be referred to as "pinch-in", and a touch operation of bringing the touch positions away from each other will be referred to as "pinch-out". The pinch-out and the pinch-in will be collectively referred to as a pinch operation (or simply "pinch"). As the touch panel 70a, a touch panel of any of the following various types may be used: a resistive touch panel, a capacitive touch panel, a surface acoustic wave touch panel, an infrared touch panel, an electromagnetic induction type touch panel, an image recognition type touch panel, and an optical sensor type touch panel. Depending on the types, some touch panels detect a touch upon detecting contact with the touch panels while the other touch panels detect a touch upon detecting the proximity of a finger or a stylus to the touch panels. A touch panel of any type of them may be used.

If a Touch-Move operation is performed in the eye-proximity state, the user can set a method for designating a position of position coordinates corresponding to the Touch-Move operation, to either absolute position designation or relative position designation. For example, if position coordinates are set to an AF frame, in the case of the absolute position designation, if the touch panel 70a is touched, an AF position associated with the touched position (position for which coordinates has been input) is set. In other words, position coordinates at which a touch operation has been performed, and position coordinates on the display unit 28 are associated. On the other hand, in the case of the relative position designation, a position coordinate at which a touch operation has been performed, and a position coordinate on the display unit 28 are not associated. In the relative position designation, irrespective of a Touch-Down position on the touch panel 70a, a touch position is moved from a currently-set AF position in a moving direction of the Touch-Move by a distance corresponding to a movement amount of the Touch-Move.

In the present exemplary embodiment, the description will be provided of processing of controlling an AF frame that is based on an eye direction input operation and a touch input operation that are performed in the digital camera 100.

Figure 3B:
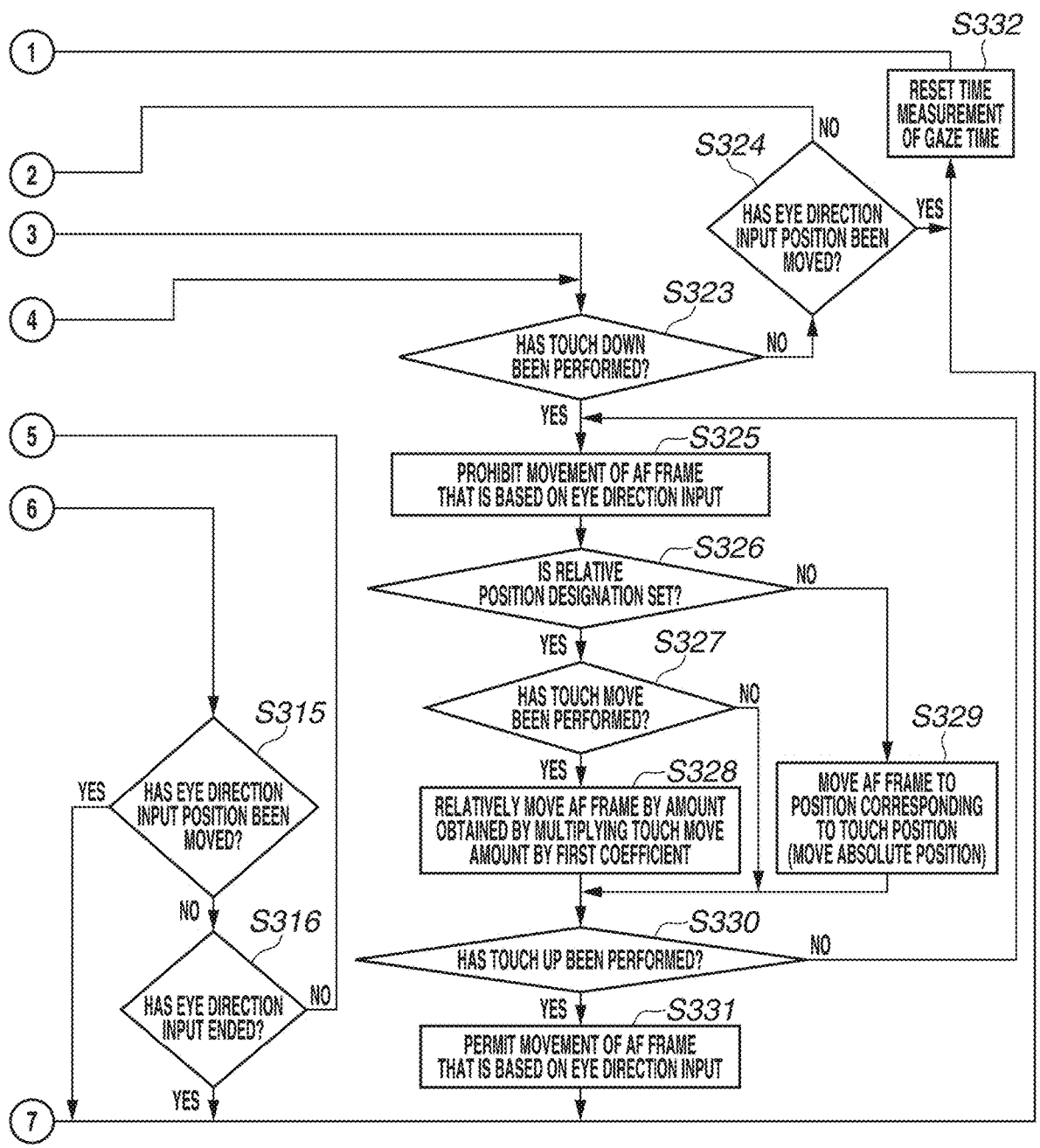

FIGS. 3A and 3B are a flowchart illustrating processing of controlling selection of a position in an AF frame based on the eye direction input and a touch operation. The control processing is implemented by the system control unit 50 loading a program stored in the nonvolatile memory 56 onto the system memory 52 and executing the program. The flowchart illustrated in FIGS. 3A and 3B is started when the digital camera 100 is activated in the image capturing mode and the user is looking into the viewfinder in the image capturing standby state, that is to say, when the eye is in proximity to the eyepiece unit 16.

Figure 4:
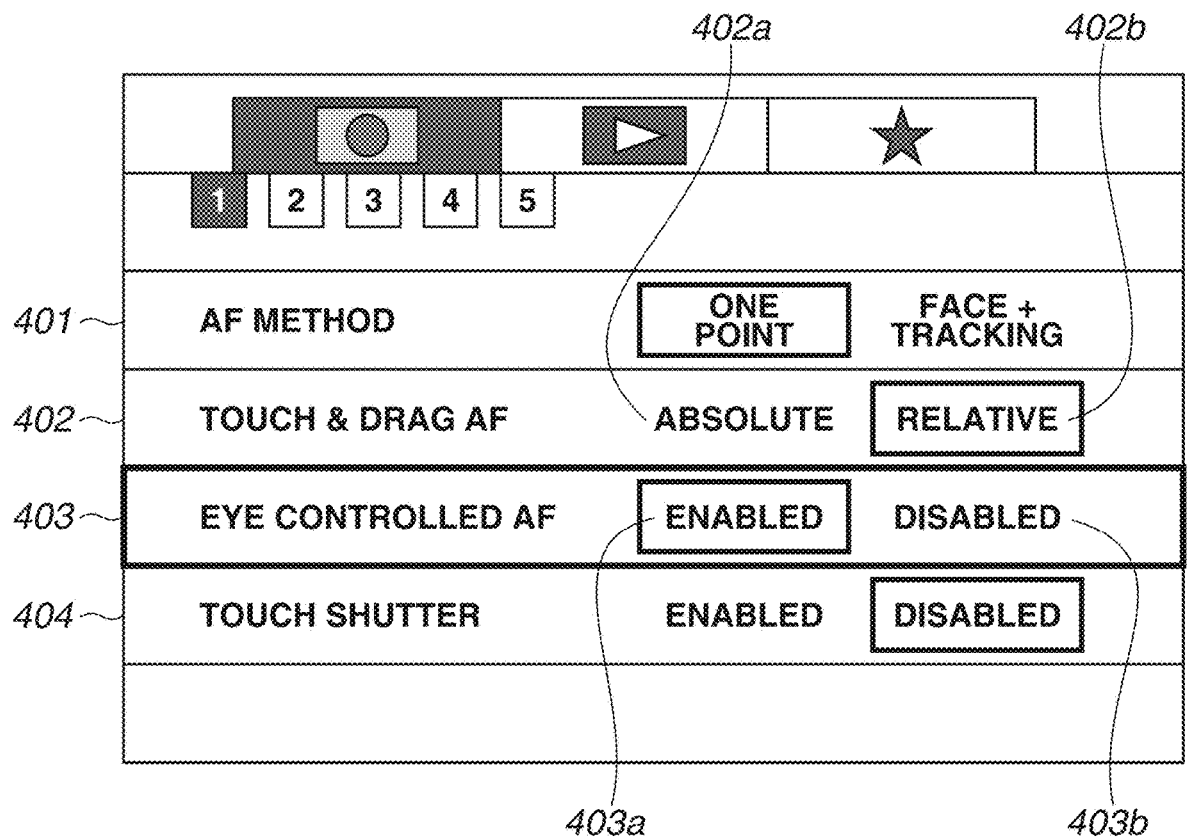
FIG. 4 illustrates a display example of a setting screen related to AF according to an exemplary embodiment of the present invention.

In step S301, the system control unit 50 determines whether the user has performed a setting change operation related to a touch operation on the touch panel 70a, in the digital camera 100. If the setting change operation has been performed (YES in step S301), the processing proceeds to step S302. If the setting change operation has not been performed (NO in step S301), the processing proceeds to step S303. Specifically, the system control unit 50 determines whether an operation of displaying a menu screen of the digital camera 100 as illustrated in FIG. 4 has been performed, and a setting change of a setting item 402 related to touch & drag AF has been performed. FIG. 4 illustrates a setting menu screen related to image capturing which is displayed on the EVF 29 or the display unit 28. On the menu screen, setting items 401 to 404 are displayed. Among the setting items, the setting item 402 relates to touch & drag AF. The touch & drag AF refers to a function regarding a way of moving an AF frame if the user performs a touch operation on the touch panel 70a while looking into the viewfinder. The user can optionally set the setting item 402. If a setting item 402a is selected, the touch & drag AF setting can be set to an absolute position designation. If a setting item 402b is selected, the touch & drag AF setting can be set to a relative position designation. FIG. 4 illustrates a state in which the setting related to the touch & drag AF is set to the relative position designation.

In step S302, the system control unit 50 stores the setting changed in step S301, into the nonvolatile memory 56.

In step S303, the system control unit 50 determines whether the user has switched the setting related to the eye direction input in the digital camera 100. If the user has switched the setting (YES in step S303), the processing proceeds to step S304. If the user has not switched the setting (NO in step S303), the processing proceeds to step S305. Specifically, the system control unit 50 determines whether an operation of displaying the menu screen of the digital camera 100 as illustrated in FIG. 4 has been performed, and a switching operation of the setting item 403 related to eye controlled AF has been performed. The eye controlled AF refers to a function regarding the movement of an AF frame that is based on the eye direction of the user. The eye controlled AF can be set to either "enabled" or "disabled". If the eye controlled AF is set to "enabled", the selection and the moving operation of an AF frame position based on the eye direction are enabled. If the eye controlled AF is set to "disabled", the selection and the moving operation of an AF frame position based on the eye direction cannot be performed. The eye controlled AF setting can be enabled by selecting a setting item 403*a*, and the eye controlled AF setting can be disabled by selecting a setting item 403*b*. FIG. 4 illustrates a state in which the eye controlled AF setting is enabled.

In step S304, the system control unit 50 stores the setting changed in step S303, into the nonvolatile memory 56.

In step S305, the system control unit 50 determines whether the eye direction input setting stored in step S304 is enabled, referring to the nonvolatile memory 56. If the eye direction input setting is enabled (YES in step S305), the processing proceeds to step S306. If the eye direction input setting is disabled (NO in step S305), the processing proceeds to step S317.

In step S306, the system control unit 50 determines the presence or absence of the eye direction input. If the eye direction input is present, that is, if an eye direction of the user has been detected in the eye tracking block 160 (YES in step S306), the processing proceeds to step S307. If the eye direction input has not been input, that is, if the eye direction of the user has not been detected in the eye tracking block 160 (NO in step S306), the processing proceeds to step S323. If the eye direction has been input, the system control unit 50 measures a time from a time point at which the eye direction input is started. In the eye tracking block 160, the eye direction position is detected, for example, every 30 milliseconds, and the detected eye direction position is sent to the system control unit 50. The system control unit 50 determines whether the user is moving his/her eye direction largely (looking around restlessly) or looking on (gazing at) a certain position, based on the eye direction position and the measured time. The gaze will be described below in step S307.

In step S307, the system control unit 50 determines whether the user is gazing. The system control unit 50 determines that the user is gazing in a case where a movement amount of the eye direction position within a predetermined time is equal to or smaller than a predetermined threshold based on the eye direction position and a measured time. For example, if a movement amount of the eye direction position within 120 milliseconds is equal to or smaller than the predetermined threshold, the system control unit 50 determines that the user is gazing. If it is determined that the user is gazing (YES in step S307), the processing proceeds to step S308. If it is determined based on the eye direction position and a measured time that the movement amount of the eye direction position is equal to or larger than the predetermined threshold, that is, if the user is moving his/her eye direction largely, the system control unit 50 determines that the user is not gazing. If it is determined that the user is not gazing (NO in step S307), the processing proceeds to step S323. In this example, gaze is used as a condition for determining the eye direction position intended by the user, in the movement of a display position of a focus detection region (hereinafter, referred to as an "AF frame") that is based on the eye direction input, but a blink of a user's eye or a voice instruction may be used as a condition. Alternatively, an AF frame may be moved in accordance with a detected position of the eye direction without detecting gaze (i.e., step S307 may be omitted and the processing may proceed to step S308 from YES in step S306). In addition, a measured time for determining gaze is set to 120 milliseconds as a specific example, but the measured time may be preset or may be freely-settable by the user, or may vary in accordance with a positional relationship between a displayed eye direction position and a gaze position.

In step S308, the system control unit 50 moves a display position of an AF frame to the eye direction (gaze) position detected in the EVF 29. In the present exemplary embodiment, the system control unit 50 moves a display position of an AF frame to the eye direction position detected in a case where a Touch-Down operation determined in step S309 is not performed, or the eye direction position detected at a start time point of the Touch-Down operation. The AF frame can be thereby swiftly moved with the eye direction even if the AF frame position detected before an operation is performed on the touch panel 70*a* and an AF frame position desired by the user are largely separated from each other.

In step S309, the system control unit 50 determines the presence or absence of Touch-Down on the touch panel 70*a*. If the Touch-Down has been performed (YES in step S309), the processing proceeds to step S310. If the Touch-Down has not been performed (NO in step S309), the processing proceeds to step S315. In the present exemplary embodiment, a control process of moving the AF frame position to a position based on the eye direction and displaying the AF frame at the position in step S308, and then, checking the presence or absence of Touch-Down is performed, but the control process is not limited to this. To prevent the user from being bothered by a displayed AF frame constantly moving based on the movement of the eye direction, the AF frame may not be moved in accordance with the eye direction before the Touch-Down, and an AF frame may be moved to the eye direction position after the Touch-Down. In other words, a control flow of performing the processing in step S308 and the processing in step S309 in a reverse order may be performed.

In step S310, the system control unit 50 temporarily prohibits (restricts) the movement of the AF frame position that is based on the eye direction input. This is because the user performs a touch operation presumably to make a fine adjustment of the AF frame position moved based on the eye direction input, during an operation performed by the user after a touch operation start. While the AF frame movement that is based on the eye direction input is prohibited (restricted), even if the gaze is detected, the AF frame movement that is based on the eye direction position is not performed. This can prevent the AF frame position finely adjusted by the user by the touch operation, from being moved to another position based on the eye direction.

In step S311, the system control unit 50 determines the presence or absence of Touch-Move on the touch panel 70*a*. If the Touch-Move has been performed (YES in step S311), the processing proceeds to step S312. If the Touch-Move has not been performed (NO in step S311), the processing proceeds to step S313.

In step S312, on the EVF 29, the system control unit 50 relatively moves the AF frame displayed on a subject image, by a second amount obtained by multiplying an amount of the Touch-Move operation performed on the touch panel 70a by a second coefficient. The second coefficient and the second amount will be described below with reference to FIGS. 5A to 5F.

In step S313, the system control unit 50 determines the presence or absence of Touch-Up from the touch panel 70a. If the Touch-Up has been performed (YES in step S313), the processing proceeds to step S314. If the Touch-Up has not been performed (NO in step S313), the processing returns to step S311.

In step S314, the system control unit 50 permits (cancels temporary prohibition/restriction of) the movement of the AF frame that is based on the eye direction input. This means permitting (cancelling restriction of) the movement of the AF frame that is based on the eye direction input that has been temporarily prohibited (restricted) in step S310, and receiving the eye direction input again (moving an AF frame based on a gaze position). This is because it is considered that a conflict between the eye direction input and the touch operation as described in step S310 does not occur because the touch operation ends by the Touch-Up determined to be performed in step S313.

In step S315, the system control unit 50 determines whether the position of the eye direction input that is detected when the Touch-Down is not performed has moved by the above-described predetermined threshold or more from the eye direction position detected when it is determined in step S307 that the user is gazing. More specifically, if an amount of movement from the gaze position determined in step S307 is equal to or larger than the predetermined threshold, it is determined that the eye direction (gaze) position has moved, and it is determined that the user is no longer gazing.

In step S316, the system control unit 50 determines whether the eye direction input has ended. If the eye direction of the user has not been detected in the eye tracking block 160, the system control unit 50 determines that the user has ended the eye direction input (YES in step S316), and the processing proceeds to step S332. If the eye direction of the user is detected in the eye tracking block 160, the system control unit 50 determines that the eye direction input continues (NO in step S316), the processing returns to step S309.

In step S317, the system control unit 50 determines the presence or absence of Touch-Down on the touch panel 70a when the eye direction input setting is disabled. If the Touch-Down has been performed (YES in step S317), the processing proceeds to step S318. If the Touch-Down has not been performed (NO in step S317), the processing returns to step S305.

In step S318, referring to the nonvolatile memory 56, the system control unit 50 determines whether the setting related to touch-based position designation that has been stored in step S302 is set to the relative position designation. More specifically, the system control unit 50 determines whether the setting of touch & drag AF in the setting item 402 is set to the relative position designation on the menu setting screen illustrated in FIG. 4. If the setting is set to the relative position designation (YES in step S318), the processing proceeds to step S319. If the setting is not set to the relative position designation (if the setting is set to the absolute position designation) (NO in step S318), the processing proceeds to step S321.

In step S319, the system control unit 50 determines the presence or absence of a Touch-Move operation on the touch panel 70a. If the Touch-Move has been performed (YES in step S319), the processing proceeds to step S320. If the Touch-Move has not been performed (NO in step S319), the processing proceeds to step S322.

In step S320, on the EVF 29, the system control unit 50 relatively moves the position of the AF frame by a first amount obtained by multiplying an amount of the Touch-Move operation on the touch panel 70a by a first coefficient. The first coefficient and the first amount will be described below with reference to FIGS. 5A to 5F.

In step S321, the system control unit 50 moves the AF frame to a position on the EVF 29 that corresponds to a touch operation position on the touch panel 70a (absolute position designation). The AF frame thereby moves to a position corresponding to a Touch-Down position in accordance with the Touch-Down, and then, the AF frame moves to a position corresponding to a touch position moved by the Touch-Move.

In step S322, the system control unit 50 determines the presence or absence of Touch-Up from the touch panel 70a. If it is determined that the Touch-Up has been performed (YES in step S322), the processing proceeds to step S305. If it is determined that the Touch-Up has not been performed (NO in step S322), the processing returns to step S318.

In step S323, the system control unit 50 determines the presence or absence of Touch-Down on the touch panel 70a. If the Touch-Down has been performed (YES in step S323), the processing proceeds to step S325. If the Touch-Down has not been performed (NO in step S323), the processing proceeds to step S324.

If it is determined in step S323 that the Touch-Down has not been performed, in step S324, the system control unit 50 determines whether the eye direction position input by the user has moved, similarly to step S315. If the eye direction input position has moved (YES in step S324), the processing proceeds to step S332. If the eye direction input position has not moved (NO in step S324), the processing proceeds to step S306.

In step S325, the system control unit 50 temporarily prohibits (restricts) the movement of the AF frame based on the eye direction input, as in step S310.

In step S326, the system control unit 50 determines whether the setting related to touch-based designation on the touch panel 70a (the setting of touch & drag AF in the setting item 402 illustrated in FIG. 4) is set to the relative position designation, as in step S318. If the setting is set to the relative position designation (YES in step S326), the processing proceeds to step S327. If the setting is not set to the relative position designation (if the setting is set to the absolute position designation) (NO in step S326), the processing proceeds to step S329.

In step S327, the system control unit 50 determines the presence or absence of the Touch-Move operation on the touch panel 70a. If it is determined that the Touch-Move has been performed (YES in step S327), the processing proceeds to step S328. If it is determined that the Touch-Move has not been performed (NO in step S327), the processing proceeds to step S330.

In step S328, on the EVF 29, the system control unit 50 relatively moves the position of the AF frame by the first amount obtained by multiplying an amount of the Touch-Move operation performed on the touch panel 70a by the first coefficient, as in step S320.

In step S329, the system control unit 50 moves the AF frame to a position on the EVF 29 that corresponds to a touch operation position on the touch panel 70a (absolute position designation), as in step S321.

In step S330, the system control unit 50 determines the presence or absence of Touch-Up from the touch panel 70a. If the Touch-Up has been performed (YES in step S330), the processing proceeds to step S331. If the Touch-Up has not been performed (NO in step S330), the processing returns to step S325.

In step S331, the system control unit 50 permits (cancels temporary prohibition/restriction of) the movement of the AF frame that is based on the eye direction input, as in step S314.

In step S332, the system control unit 50 resets a time measured by a timer until it is determined that the gaze is started in step S306, and the processing returns to step S305.

If the first shutter switch 62 is turned on during the control process illustrated in FIGS. 3A and 3B, AF is performed at the AF frame position displayed at the time point. More specifically, if the AF frame position is displayed based on the eye direction, AF is performed at the AF frame position displayed based on the eye direction. If the AF frame position based on the eye direction is not displayed, AF is performed at the AF frame position displayed before the touch operation. If the first shutter switch 62 is turned on during a Touch-Move operation, AF is performed at a displayed AF frame position. If the second shutter switch 64 is turned on during the control process, AF is performed using an AF frame displayed at a time point at which the second shutter switch 64 is turned on, and image capturing is performed.

In addition, the flowchart illustrated in FIGS. 3A and 3B is processing which is performed in a case where an eye in the proximity to the eyepiece unit 16 is detected by the eye-proximity detection unit 57. In a case where the eye-proximity detection unit 57 does not detect an eye in the proximity to the eyepiece unit 16, a live view image is displayed on the display unit 28. At this time, the system control unit 50 moves the AF frame to a touch position in accordance with the Touch-Down without following the setting related to position designation that is based on a touch operation (the touch & drag AF setting in FIG. 4). In other words, in a case where the eye in the proximity to the eyepiece unit 16 is not detected, the AF frame is not moved based on the eye direction, and the AF frame is moved based on the absolute position designation that is based on a touch operation.

The position movement of an AF frame that is performed through the processing illustrated in FIGS. 3A and 3B will be described with reference to FIGS. 5A to 5F.

Figure 5A:
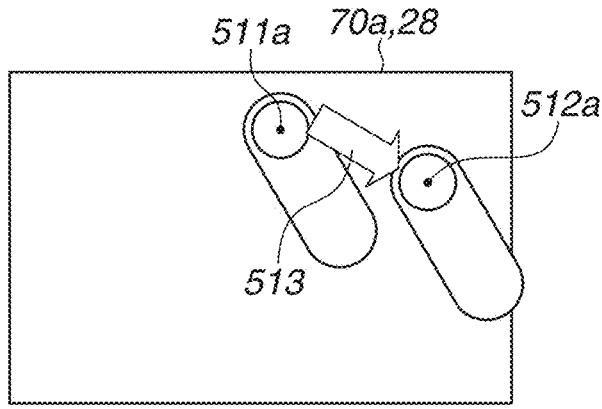
FIGS. 5A, 5B, 5C, 5D, 5E, and 5F illustrate display examples in which a display position of an AF frame is moved based on the eye direction input and a touch operation according to an exemplary embodiment of the present invention.
Figure 5B:
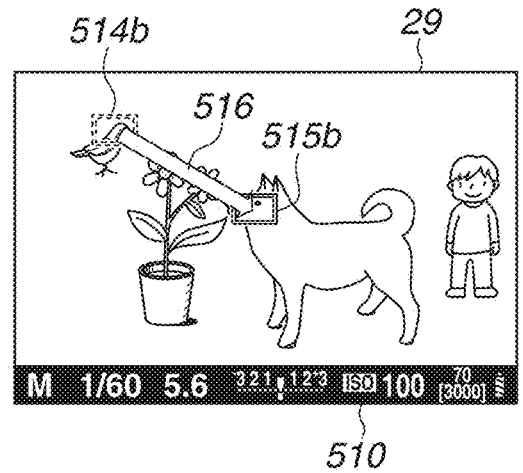

FIG. 5A illustrates an example of an operation which is performed on the touch panel 70a in a case where an eye direction is not input by the user (in a case where the eye direction input setting is disabled, or the eye direction input setting is enabled and no eye direction (gaze) input is provided to the eye tracking block 160), and in a case where the setting related to touch-based position designation is set to the relative position designation. FIG. 5B illustrates a display example of an AF frame on the EVF 29 that corresponds to the operation example illustrated in FIG. 5A. A touch position 511a illustrated in FIG. 5A is a Touch-Down position input by the user, and a touch position 512a is a touch position set after a Touch-Move operation performed after the Touch-Down is performed at the touch position 511a. An AF frame 514b illustrated in FIG. 5B is a display position (selected position) of the AF frame set before the Touch-Down, and an AF frame 515b is a display position of the AF frame that is set after the Touch-Move operation performed after the Touch-Down is performed. The respective position coordinates of these positions are defined as follows:

Pt1 (X1, Y1): Touch-Down position (511a),
Pt2 (X2, Y2): touch position (512a) set after Touch-Move,
Ps1 (x1, y1): position (514b) of AF frame that is set before Touch-Down, and
Ps2 (x2, y2): position (515b) of AF frame that is set after Touch-Move.

In this case, the system control unit 50 calculates an x-coordinate and a y-coordinate of Ps2 as follows, and displays the AF frame at the calculated position Ps2 (operations in steps S318 and S325 of FIG. 3B):

$$x2=x1+A1(X2-X1);$$

$$y2=y1+A1(Y2-Y1); \text{ and}$$

A1: first coefficient.

In such a manner, the AF frame is moved by the first amount obtained by multiplying the Touch-Move operation amount by the first coefficient (A1). If the first coefficient A1 is a coefficient large to some extent, even when a Touch-Move operation amount is small, it is possible to reduce the number of reciprocating operations of a finger, and move the AF frame to a desired position more swiftly. The AF frame is moved based on a small Touch-Move amount, and thus, it is difficult to finely adjust the position of the AF frame to a position desired by the user.

Figure 5C:
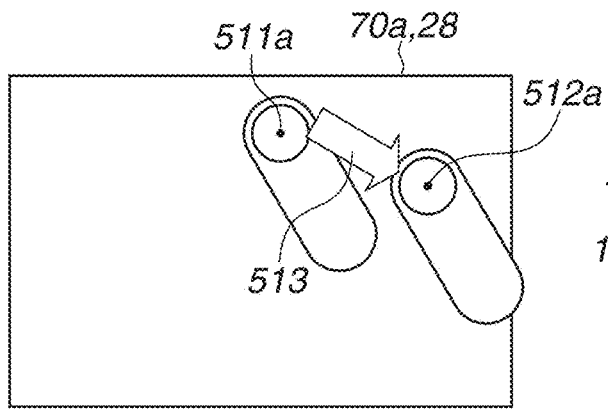
Figure 5D:
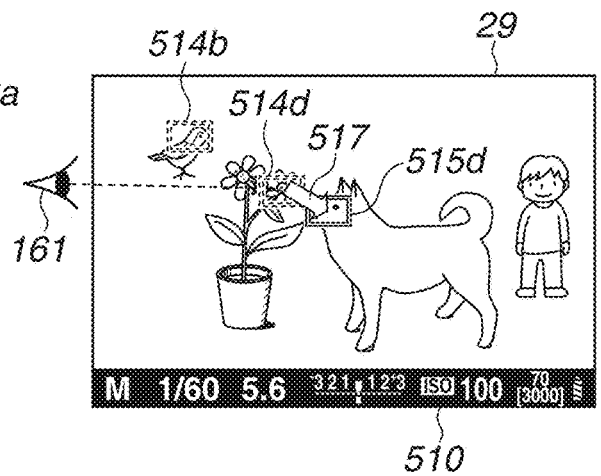

Next, FIG. 5C illustrates an example of an operation performed on the touch panel 70a in a case where the eye direction input by the user is present (if the eye direction input setting is enabled and it is determined that the user is gazing). FIG. 5D illustrates a display example of the AF frame on the EVF 29 that corresponds to the operation example illustrated in FIG. 5C. Touch positions 511a and 512a illustrated in FIG. 5C have the same position coordinates as those of the touch positions illustrated in FIG. 5A. An AF frame 514b illustrated in FIG. 5D is a display position of the AF frame set before the AF frame is moved based on the eye direction input. An AF frame 514d is a display position of an AF frame based on the eye direction input, and an AF frame 515d is a display position of the AF frame that has been further moved by a Touch-Move operation performed after the AF frame is moved based on the eye direction input. The respective position coordinates of the touch positions 511a and 512a and the AF frames 514d and 515d are defined as follows:

Pt1 (X1, Y1): Touch-Down position (511a),
Pt2 (X2, Y2): touch position (512a) set after Touch-Move,
Ps3 (x3, y3): position (514d) of AF frame that is based on eye direction input, and
Ps4 (x4, y4): position (515d) of AF frame that is set after Touch-Move performed after eye direction input.

In this case, the system control unit 50 calculates an x-coordinate and a y-coordinate of Ps4 as follows, and displays the AF frame at the calculated position Ps4 (processing in step S312 of FIG. 3A):

$$x4=x3+A2(X2-X1);$$

$$y4=y3+A2(Y2-Y1); \text{ and}$$

A2: second coefficient (smaller than first coefficient (A2<A1)).

In this manner, initially, the AF frame can be swiftly moved, based on the eye direction input, from the original position of the AF frame 514b to the position of the AF frame 514d near the position desired by the user (the processing in step S308 of FIG. 3A). The AF frame displayed on the subject image is then moved from the eye direction position by the second amount obtained by multiplying a Touch-Move operation amount by the second coefficient (A2) smaller than the first coefficient (A1). Because the second coefficient A2 is smaller than the first coefficient A1 (A2<A1), the AF frame is not moved by a large Touch-Move operation amount, and if Touch-Move operation amounts are the same, the AF frame can be moved finely by the second amount smaller than the above-described first amount. In other words, after a rough movement of the AF frame position is performed based on the eye direction, fine adjustment of the AF frame position can be performed by a Touch-Move operation. Thus, the position of the AF frame can be swiftly and finely moved to the position desired by the user. In the operation in step S312, irrespective of whether the setting related to touch-based position designation that has been stored in step S302 is set to the relative position designation or the absolute position designation, the AF frame is moved in accordance with the relative position designation. In other words, even if the user presets the absolute position designation, the touch operation movement of the AF frame, following the movement of the AF frame based on the eye direction, is performed in accordance with the relative position designation. With this configuration, a large movement of the AF frame based on the absolute position designation does not occur after a rough position of the AF frame has been determined based on the eye direction. A large movement of the AF frame that is unintended by the user can be thereby avoided.

Figure 5E:
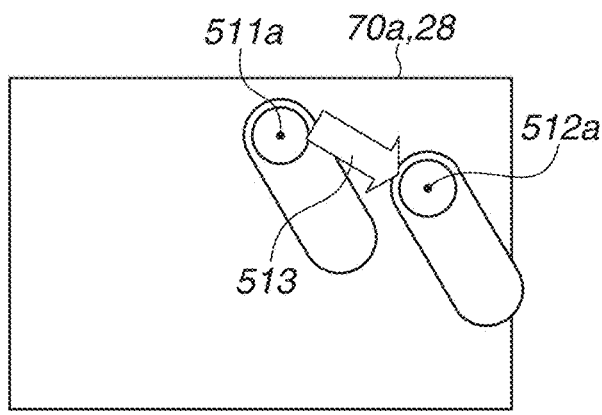
Figure 5F:
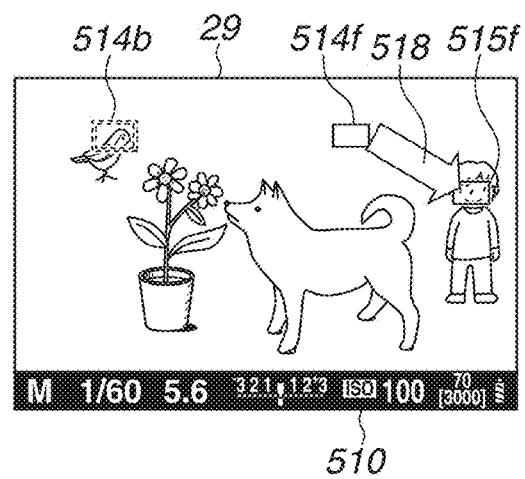

FIG. 5E illustrates an example of an operation performed on the touch panel 70a in a case where the eye direction input by the user is not present (if eye direction input setting is disabled, or eye direction input setting is enabled and the eye direction (gaze) input is absent), and in a case where the setting related to touch-based position designation is set to the absolute position designation. FIG. 5F illustrates a display example of the AF frame on the EVF 29 corresponding to the operation example illustrated in FIG. 5E. Touch positions 511a and 512a illustrated in FIG. 5E are the same positions as the touch positions illustrated in FIG. 5A. An AF frame 514b illustrated in FIG. 5F is a display position of an AF frame that is set before the Touch-Down, and is the same position as the AF frame 514b illustrated in FIG. 5B. An AF frame 514f is a display position of an AF frame displayed at a position corresponding to a Touch-Down position. An AF frame 515f is an AF frame display position set after a Touch-Move operation. In FIGS. 5E and 5F, the setting related to touch-based position designation is set to the absolute position designation. Thus, a touch position and the AF frame displayed on the EVF 29 are displayed in association with each other. The respective coordinates of these positions can be therefore represented as follows:

Pt1 (X1, Y1): Touch-Down position (511a),
Pt2 (X2, Y2): touch position (512a) set after Touch-Move,
Ps5 (x5, y5): AF frame position (514f) based on Touch-Down position, and
Ps6 (x6, y6): AF frame position (515f) is based on touch position after Touch-Move.

The AF frame is displayed at the position coordinates Ps5 and Ps6 through the operation in step S329 of FIG. 3B.

Here, because the position coordinates Pt1 and Ps5 are associated and the position coordinates Pt2 and Ps6 are associated, a movement ratio on the touch panel 70a of a movement amount 513 indicated by an arrow illustrated in FIG. 5E is the same as a movement ratio on the EVF 29 of a movement amount 518 indicated by an arrow illustrated in FIG. 5F. The position coordinates Ps5 and Ps6 are not affected by the position of the AF frame 514b that is set before the Touch-Down.

In this manner, a method for moving a display position of an AF frame using the touch panel 70a is controlled in accordance with the presence or absence of the eye direction input in the present exemplary embodiment. The AF frame can be thereby swiftly moved to a position desired by the user even in a case where the eye direction input is absent. In a case where the eye direction input is present, the AF frame can be swiftly moved to the position desired by the user based on the eye direction, and the AF frame can be finely adjusted in accordance with a Touch-Move operation.

Figure 6A:
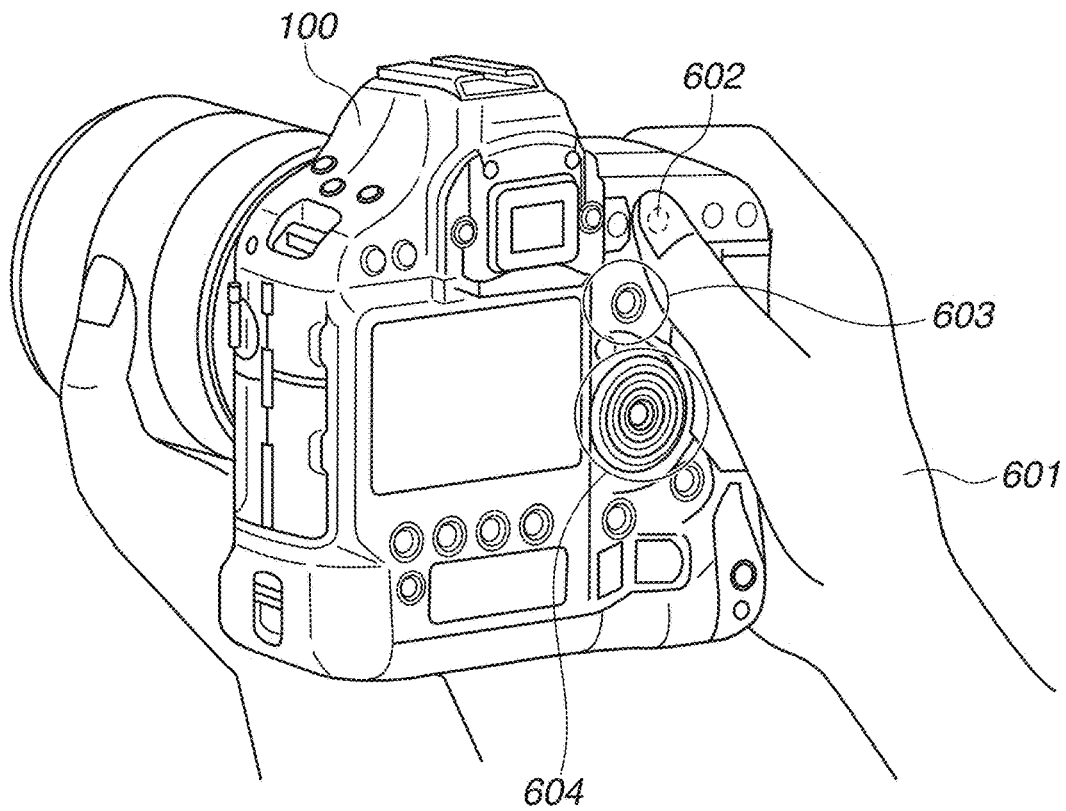
FIGS. 6A and 6B are diagrams each illustrating an exemplary embodiment in a case of using another operation member or a case of not using a viewfinder according to an exemplary embodiment of the present invention.
Figure 6B:
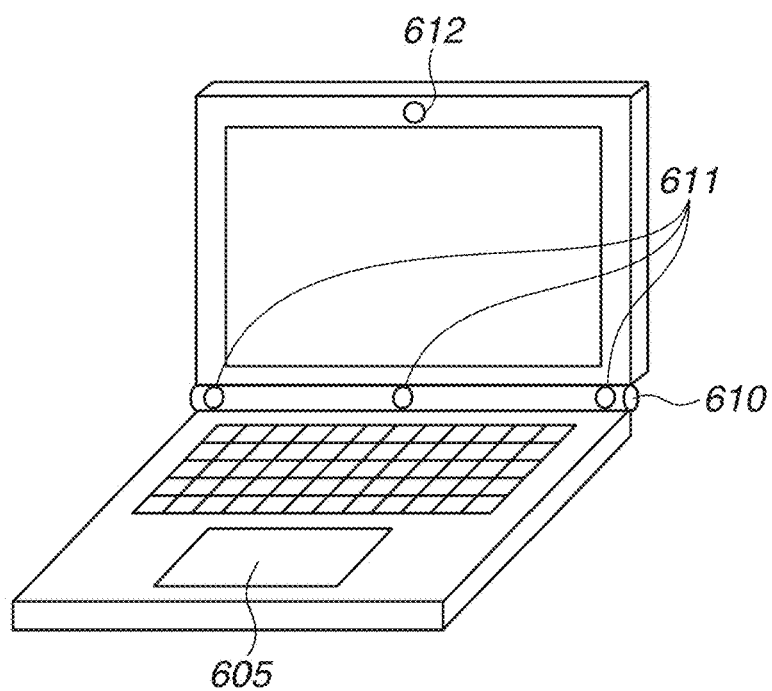

In the above-described exemplary embodiment, the description has been provided of an example in which the eye direction of the user looking into the viewfinder is detected, and position designation is performed in combination with the position designation operation using the touch panel, but the configuration is not limited to this. FIGS. 6A and 6B illustrate an exemplary embodiment in the case of using another operation member other than the touch operation member in the present exemplary embodiment, and an exemplary embodiment in the case of not using the EVF 29.

FIG. 6A illustrates an example of moving an AF frame using another operation member that can input an eye direction and is other than the EVF 29 and the touch operation member. More specifically, the operation member includes an optical tracking pointer (OTP) 602, a directional key (multi-controller) 603 operable in eight directions, and a dial 604. The optical tracking pointer is a type of a pointing device, and is mainly employed in a laptop computer (an example in which the optical tracking pointer is mounted on the digital camera 100 is illustrated in the present exemplary embodiment). As a physical outlook, the optical tracking pointer is a short stick-shaped button. The optical tracking pointer issues an operation instruction when a finger moves over a head portion, which is a member surface. Infrared light or another type of light is emitted from an internal light source such as a light-emitting diode (LED) onto the head portion, and light reflected by the finger is received as a signal. The movement of the finger is thereby detected and used as an operation instruction.

In FIG. 6A, the user holds the digital camera 100 with a hand 601 and operates the OTP 602 with the thumb. By moving the finger over the OTP 602 while looking into a viewfinder, an operation equivalent to a Touch-Move operation in the present exemplary embodiment can be performed. Specifically, if the eye direction input is absent, an AF frame is relatively moved by the first amount obtained by multiplying an operation amount of Touch-Move of moving the finger over the OTP 602, by the first coefficient. In addition, in a case where the eye direction input is present after the AF frame is moved based on the eye direction, the AF frame is relatively moved by the second amount (smaller than the first amount when Touch-Move amounts are the same) obtained by multiplying an operation amount of Touch-Move performed on the OTP 602 by the second coefficient (<first coefficient). The second amount is a movement amount that cannot move the AF frame from the end of the screen of the touch panel 70a to the other end only by a single touch operation on the touch panel 70a.

The display position of the AF frame in the viewfinder based on the presence or absence of the eye direction input and an OTP operation is moved in a manner similar to the one in the processing described in the present exemplary embodiment with reference to FIGS. 3A and 3B and 5A to 5F. The OTP 602 has been described as an example of another operation member corresponding to the touch operation member, but the directional key 603, the dial 604, or each directional press button of the cross key 74 illustrated in FIG. 1 also functions in a similar manner. In these members, an operation of pressing down (pressing in) the directional key 603 or the cross key 74 once in a certain direction, or an operation of continuously pressing down (pressing in) the directional key 603 or the cross key 74 for a predetermined time or more corresponds to the above-described Touch-Move operation. For example, the AF frame is moved by a movement amount obtained by multiplying the number of times the directional key 603 or the cross key 74 is pressed in, by the above-described first coefficient or second coefficient. Alternatively, for example, the AF frame is moved by a movement amount obtained by multiplying a duration time of pressing by the above-described first coefficient or second coefficient. Alternatively, an operation of rotating a rotatory portion of the dial 604 corresponds to the above-described Touch-Move operation. More specifically, an AF frame is moved by a movement amount obtained by multiplying a rotation amount by the above-described first coefficient or second coefficient.

FIG. 6B illustrates an example of moving a mouse pointer using a trackpad of a laptop computer. FIG. 6B illustrates a trackpad 605 as a component equivalent to the touch panel 70*a* described in the present exemplary embodiment. An independent eye tracking device 610 is connected to the laptop computer as the eye tracking block 160 of the laptop computer, and the eye direction position is determined using cameras 611 mounted on the eye tracking device 610 and an onboard camera 612 built in the laptop computer. As in the laptop computer, if the eye direction input is not present, by the user performing a Touch-Move operation on the trackpad 605, a mouse pointer displayed on a monitor can be relatively moved by the first amount as in the present exemplary embodiment. If the eye direction input is present, the mouse pointer moves to the eye direction position in accordance with the eye direction input. In accordance with a Touch-Move operation on the trackpad 605, the mouse pointer displayed at the eye direction position is relatively moved by the second amount (smaller than the first amount when Touch-Move amounts are the same) obtained by multiplying an operation amount of Touch-Move by the second coefficient (<first coefficient). The mouse pointer can be thereby finely adjusted also by the trackpad 605.

FIG. 6B illustrates the laptop computer as another exemplary embodiment, but the touch operation member is not limited to the trackpad 605 of the laptop computer. For example, a mouse, a pointing device, or a joystick can also be applied to the present exemplary embodiment. The trackpad, the mouse, the pointing device, and the joystick may not be built into a laptop computer and may be externally attached.

In addition, a touchpad or a joystick that is mounted on a remote controller, such as a pointer can also perform a position movement instruction operation equivalent to a Touch-Move operation or Touch-Move as in the present exemplary embodiment. In this case, the eye tracking block 160 is mounted on or connected to an external monitor or a projector. In addition, the eye direction detection sensor may exist independently of the external monitor, the projector, and the pointer.

As described above, if a display position is not moved based on the eye direction input and the setting related to touch-based position designation is the relative position designation, in accordance with an operation amount of an operation member, the display position is relatively moved from the position set before the operation, by the first amount obtained by multiplying the operation amount by the first coefficient. If the setting related to touch-based position designation is the absolute position designation, the display position is moved to a position corresponding to an operation position at which an operation on an operation member is started. If a display position is moved based on the eye direction input, based on an operation amount of an operation member, the display position is relatively moved from the eye direction position by the second amount obtained by multiplying the operation amount by the second coefficient smaller than the first coefficient. With this configuration, in a case where the setting related to touch-based position designation is set to the relative position designation, and even in a case where no eye direction input is present, the AF frame is moved by the first amount larger than the second amount in response to an operation on an operation member. Thus, the display position can be swiftly moved to a position desired by the user. In a case where the eye direction input is present, the display position can be swiftly moved to the position desired by the user based on the eye direction, and thus, the display position can be finely adjusted in response to an operation on the operation member. In a case where the setting related to touch-based position designation is set to the absolute position designation in a case where no eye direction input is present, the AF frame is moved to a position corresponding to an operation position of the operation member. The display position can be thus swiftly moved to the position desired by the user. In a case where the eye direction input is present, irrespective of whether the setting related to touch-based position designation is set to the absolute position designation or the relative position designation, the relative position designation is employed, and the display position is moved by the second amount in response to an operation on the operation member. With this configuration, the display position can be swiftly moved to the position desired by the user based on the eye direction, and the display position can be finely adjusted in response to an operation on the operation member without generating a large movement of the display position in accordance with the absolute position designation.

The above-described various types of control described to be performed by the system control unit 50 may be performed by a single hardware device, or the entire apparatus may be controlled by a plurality of hardware devices (e.g., a plurality of processors or circuits) sharing the processing.

The exemplary embodiments of the present invention have been described in detail, but the present invention is not limited to these specific exemplary embodiments, and various configurations are also included in the present invention without departing from the spirit of the invention. The touch panel 70*a* has been described as an example of an instruction member of position movement that is to be used in combination with the eye direction input, but another operation member other than the touch panel 70*a*, such as a button or a dial may be used. The display position is treated as the AF frame, but the display position may be an icon frame or a parameter setting frame, or an indicator display, such as a mouse pointer, different from the AF frame. A time measured from when the eye direction input to the eye tracking block 160 has started is used as a determination standard of gaze, but the measured time may be a preset time. The time may vary in accordance with a positional relationship between a displayed AF frame and the eye direction position, or may be optionally-settable by the user. In the present exemplary embodiment, gaze is used as a determination standard of the eye direction position intended by the user, but the eye direction position may not be determined based on gaze, and may be determined only based on whether the eye direction input setting (the eye direction controlled AF in the setting item 403 in FIG. 4) is enabled or disabled.

In the above-described exemplary embodiments, an example in which the present invention is applied to a digital camera has been described, but an application example is not limited to this example. The present invention can be applied to any electronic apparatus as long as the electronic apparatus includes a reception unit that receives the eye direction input. In addition, the exemplary embodiments can also be appropriately combined. In the present exemplary embodiment, the EVF 29 and the eye tracking are used, but the present exemplary embodiment can be implemented also in a configuration in which a display device and eye tracking are used. More specifically, the present invention can be applied to a personal computer, a personal digital assistance (PDA), a mobile phone terminal, a portable image viewer, a printing apparatus including a display, a digital photo frame, a music player, a game machine, an electronic book reader, or a wearable device, such as a head-mounted display.

An application example is not limited to an imaging apparatus main body, and the present invention can also be applied to a control apparatus that communicates with an imaging apparatus (including a network camera) via wired or wireless communication, and remotely controls the imaging apparatus. Examples of the control apparatus that remotely controls the imaging apparatus include a smartphone, a tablet personal computer (PC), and a desktop PC. By notifying commands for causing the imaging apparatus to perform various operations and settings, from the control apparatus based on operations performed by the control apparatus or processing performed by the control apparatus, the imaging apparatus can be remotely controlled. In addition, the control apparatus may receive a live view image captured by the imaging apparatus, via wired or wireless communication, and display the live view image.

According to an exemplary embodiment of the present invention, a selected position can be moved swiftly and accurately to a position desired by the user.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2019-112314, filed Jun. 17, 2019, which is hereby incorporated by reference herein in its entirety.

What is claimed is:

1. An apparatus comprising:
one or more processors; and
one or more memories storing instructions that, when executed by the one or more processors, cause the apparatus to perform operations comprising:
receiving an eye direction input that is an input based on an eye tracking process; and
controlling movement of a display position based on an operation on an operation member,
wherein the display position is moved by a first amount or a second amount and from, respectively, a first position or a second position depending on whether the apparatus is operating in a first state or second state with respect to eye direction input, and
wherein
in the first state, the display position is not designated based on the eye direction input, and, in response to the operation member being operated by a predetermined movement amount, the display position is moved by the first amount from the first position, the first position being a position the display position was set to before the operation member was operated, and
in the second state, the display position is designated based on the eye direction input, and, in response to the operation member being operated by the predetermined movement amount, the display position is moved by the second amount from the second position, the second position being designated based on the received eye direction input, before the operation member was operated, and the first amount being larger than the second amount.

2. The apparatus according to claim 1,
wherein the operations further comprise:
setting a setting to any one of a plurality of settings including:
a first setting of moving, in response to the operation member being operated by the predetermined movement amount, the display position by a predetermined amount based on a first position set before the operation member is operated, from the first position set before the operation, and
a second setting of moving, in response to the operation member being operated, the display position to a second position corresponding to an operation position at which an operation on the operation member is started, irrespective of the first position set before the operation,
wherein, in the second state, the control is performed such that the display position is moved by the second amount from the first position set before the operation, in response to the operation with the predetermined movement amount, irrespective of what setting is set by the apparatus in the setting step.

3. The apparatus according to claim 2,
wherein, in a case where the setting related to an operation on the operation member is set to the first setting in the first state, in response to the operation member being operated by the predetermined movement amount, the control is performed such that the display position is moved by the first amount based on the first position set before the operation member is operated, from the first position set before the operation, and
wherein, in a case where the setting related to an operation on the operation member is set to the second setting in the first state, in response to the operation member being operated, the control is performed such that the display position is moved to the second position corresponding to the operation position at which the operation on the operation member is started, irrespective of the display position set before the operation.

4. The apparatus according to claim 1, wherein the operations further comprise displaying an indicator indicating that a displayed position is the display position, at the display position.

5. The apparatus according to claim 4, wherein the indicator is displayed in response to the operation member being operated by a user.

6. The apparatus according to claim 1, wherein the control is performed such that the display position is moved based on the eye direction input in a case where the operation member is not being operated, or the eye direction input at an operation start time point, and performs control such that the display position is not moved based on the eye direction input during an operation performed after the operation is started with the operation member.

7. The apparatus according to claim 1, wherein the first state is a state in which a setting related to the eye direction input is set to a setting of not moving the display position based on the eye direction input, and the second state is a state in which the setting related to the eye direction input is set to a setting of moving the display position based on the eye direction input.

8. The apparatus according to claim 1, wherein the first state is a state in which the eye direction input is not detected by a detector configured to detect the eye direction input received by the apparatus, and the second state is a state in which the eye direction input is detected by the detector.

9. The apparatus according to claim 1, wherein the first amount is an amount obtained by multiplying the predetermined movement amount by a first coefficient, and the second amount is an amount obtained by multiplying the predetermined movement amount by a second coefficient smaller than the first coefficient.

10. The apparatus according to claim 1, wherein the second amount is a movement amount by which the display position is not moved from an end of a screen to another end of the screen with a single operation on the operation member.

11. The apparatus according to claim 1, wherein the operation member is a touch operation member configured to detect a touch operation.

12. The apparatus according to claim 1, wherein the operation member is any one of the operation member configured to calculate a moving direction and a movement amount of a finger by the finger moving over a surface of the operation member, and move the display position, a directional key operable in eight directions, a joystick, and a directional key including a press button pressable in four directions.

13. The apparatus according to claim 1, wherein the second state is a state in which a movement amount of a position at which the eye direction input is detected within a predetermined time is equal to or smaller than a predetermined threshold.

14. The apparatus according to claim 1, wherein the display position is a display position for a focus detection region.

15. The apparatus according to claim 1, further comprising:
an image sensor;
a viewfinder; and
a display in the viewfinder,
wherein the display position displayed on a subject image on the display can be moved by the operation member provided on an outside of the viewfinder being operated.

16. A non-transitory computer-readable storage medium storing a program for causing a computer to perform the operations that are performed by the apparatus according to claim 1.

17. A method for controlling an apparatus, the method comprising:
receiving an eye direction input that is an input based on an eye tracking process; and
controlling movement of a display position based on an operation on an operation member,
wherein the display position is moved by a first amount or a second amount and from, respectively, a first position or a second position depending on whether the apparatus is operating in a first state or second state with respect to eye direction input, and
wherein
in the first state, the display position is not designated based on the eye direction input, and, in response to the operation member being operated by the predetermined movement amount, the display position is moved by the first amount from the first position, the first position being a position the display position was set to before the operation member was operated, and
in the second state, the display position is designated based on the eye direction input, and, in response to the operation member being operated by the predetermined movement amount, the display position is moved by the second amount from the second position, the second position being designated based on the received eye direction input, before the operation member was operated, and the first amount being larger than the second amount.

* * * * *